(12) United States Patent
Campagna et al.

(10) Patent No.: US 11,918,369 B2
(45) Date of Patent: Mar. 5, 2024

(54) NEUROLOGICAL AND MOTOR FUNCTION SCREENING APPARATUS

(71) Applicant: Reflexion Interactive Technologies Inc., Lancaster, PA (US)

(72) Inventors: Matthew Campagna, Lancaster, PA (US); Matthew Roda, Lancaster, PA (US); Patrick Walsh, Akron, PA (US); T Keith Ward, East Petersburg, PA (US)

(73) Assignee: REFLEXION INTERACTIVE TECHNOLOGIES LLC, Lancaster, PA (US)

( * ) Notice: Subject to any disclaimer, the term of this patent is extended or adjusted under 35 U.S.C. 154(b) by 502 days.

(21) Appl. No.: 17/160,095

(22) Filed: Jan. 27, 2021

(65) Prior Publication Data

US 2021/0244342 A1 Aug. 12, 2021

Related U.S. Application Data

(62) Division of application No. 15/621,068, filed on Jun. 13, 2017, now abandoned.

(51) Int. Cl.
*G06F 1/16* (2006.01)
*A61B 5/00* (2006.01)
*A61B 5/16* (2006.01)
*G06F 3/041* (2006.01)
*A61B 5/11* (2006.01)

(52) U.S. Cl.
CPC ............ *A61B 5/4064* (2013.01); *A61B 5/162* (2013.01); *A61B 5/7435* (2013.01); *G06F 1/1605* (2013.01); *G06F 3/0416* (2013.01); *A61B 5/1128* (2013.01)

(58) Field of Classification Search
CPC .............................. G06F 1/1601; G06F 1/1605
See application file for complete search history.

(56) References Cited

U.S. PATENT DOCUMENTS

| | | | | |
|---|---|---|---|---|
| 3,482,241 A | | 12/1969 | Johnson | |
| 3,909,525 A | * | 9/1975 | Fagan | H04N 3/28 345/1.3 |
| 4,110,792 A | * | 8/1978 | Long | G09F 13/28 345/55 |

(Continued)

OTHER PUBLICATIONS

Foreman, K., Baas, E., Test-Retest on the Wayne Saccadic Fixator in Professional Soccer Players, Optometry & Visual Performance, Jun. 2016, p. 103, vol. 4, Issue 3.

*Primary Examiner* — Adrian S Wilson
(74) *Attorney, Agent, or Firm* — Gould & Ratner LLP

(57) ABSTRACT

The present invention provides for a panel for receiving neurocognitive data having a collapsible and portable user interface touch screen display bounded by a frame, the touch screen display having a width that extends into a user's peripheral vision by having the touch screen display extending from 60 to 120 degrees from a center of the user's gaze. The invention provides the touch screen display mounted on a support stand at the user's eye level and a computer electronically connected to the touch screen display via a control unit, the touch screen display comprising a tactile area having touch sensing capacity. The touch screen display for receiving at least one stimulus via the electronic connection to the control unit.

20 Claims, 7 Drawing Sheets

(56) References Cited

U.S. PATENT DOCUMENTS

| | | | |
|---|---|---|---|
| 4,257,207 A * | 3/1981 | Davis | G09F 15/0068 52/631 |
| RE30,777 E * | 10/1981 | Ytter | E05D 5/0238 160/351 |
| 4,821,437 A * | 4/1989 | Abramson | G09F 3/20 40/658 |
| 5,088,810 A | 2/1992 | Galanter | |
| 5,128,662 A * | 7/1992 | Failla | G06F 1/1624 345/905 |
| 5,220,952 A * | 6/1993 | Beaulieu | G09F 15/0068 160/231.1 |
| 5,515,900 A * | 5/1996 | West | G09F 15/0068 160/230 |
| 5,812,239 A | 9/1998 | Eger | |
| 6,018,898 A * | 2/2000 | Auty | G09F 3/202 40/661 |
| 6,144,550 A * | 11/2000 | Weber | G06F 1/1652 345/905 |
| 6,377,228 B1 | 4/2002 | Jenkin | |
| 6,819,304 B2 * | 11/2004 | Branson | G06F 1/1677 345/1.3 |
| 7,091,926 B2 * | 8/2006 | Kulas | G06F 3/1446 345/1.3 |
| 7,092,247 B2 * | 8/2006 | Kim | G06F 1/1622 361/679.04 |
| 7,095,387 B2 * | 8/2006 | Lee | G06F 1/1652 345/1.3 |
| 7,359,121 B2 * | 4/2008 | French | A63B 71/0622 73/79 |
| D581,380 S * | 11/2008 | Derocher | D14/127 |
| D600,233 S * | 9/2009 | Birsel | D14/203.3 |
| 7,782,274 B2 * | 8/2010 | Manning | G06F 1/1641 345/1.3 |
| D645,467 S * | 9/2011 | Mitsuhashi | D14/374 |
| 8,432,331 B2 * | 4/2013 | Schilling | H04M 1/0247 345/905 |
| 8,508,433 B2 * | 8/2013 | Manning | G06F 3/1423 345/1.3 |
| 8,529,106 B2 * | 9/2013 | Jung | G09F 7/002 362/388 |
| 8,539,705 B2 * | 9/2013 | Bullister | G06F 1/1615 361/679.04 |
| 8,665,583 B2 * | 3/2014 | Kinsley | A47B 46/005 361/679.01 |
| 8,669,918 B2 * | 3/2014 | Manning | G06F 3/1423 345/1.3 |
| 8,907,864 B2 * | 12/2014 | Manning | G06F 1/1652 345/1.3 |
| 8,970,449 B2 * | 3/2015 | Manning | G06F 1/1677 345/1.3 |
| 9,030,812 B2 * | 5/2015 | Nakamura | G06F 1/1624 361/679.04 |
| 9,078,598 B2 * | 7/2015 | French | A61B 5/1128 |
| 9,423,829 B2 * | 8/2016 | Manning | G06F 1/1677 |
| 9,440,090 B2 * | 9/2016 | Jo | A61N 5/06 |
| 9,778,689 B2 * | 10/2017 | Song | G09F 9/00 |
| D806,051 S * | 12/2017 | Fleming, Jr. | D14/203.7 |
| 10,114,417 B2 * | 10/2018 | Manning | G06F 1/1616 |
| 10,139,879 B2 * | 11/2018 | Yamazaki | G06F 1/1635 |
| 10,444,796 B2 * | 10/2019 | Manning | G06F 1/1679 |
| 10,672,306 B1 * | 6/2020 | Whidden | G09F 15/0068 |
| 11,003,214 B2 * | 5/2021 | Manning | G06F 1/1618 |
| 11,130,001 B2 * | 9/2021 | Hong | A61N 5/0616 |
| 11,204,631 B2 * | 12/2021 | Mehandjiysky | G09F 9/301 |
| 11,474,646 B2 * | 10/2022 | Yamazaki | G06F 1/1683 |
| 11,550,363 B2 * | 1/2023 | Manning | G06F 1/1616 |
| 2003/0071832 A1 * | 4/2003 | Branson | G06F 3/1446 345/698 |
| 2003/0160735 A1 * | 8/2003 | Lee | G06F 3/147 345/4 |
| 2003/0160755 A1 * | 8/2003 | Gettemy | G06F 1/1615 345/156 |
| 2005/0088463 A1 * | 4/2005 | Schilling | G09G 3/20 345/699 |
| 2007/0044357 A1 * | 3/2007 | Biondo | G09F 13/22 40/544 |
| 2008/0242949 A1 | 10/2008 | Jung | |
| 2011/0184498 A1 | 7/2011 | Donley | |
| 2011/0205167 A1 * | 8/2011 | Massengill | A61B 5/162 345/173 |
| 2011/0279951 A1 * | 11/2011 | Kinsley | A47B 46/005 361/679.01 |
| 2018/0070843 A1 * | 3/2018 | Campagna | A61B 5/7435 |

* cited by examiner

NEUROLOGICAL AND MOTOR FUNCTION SCREENING APPARATUS

RELATED APPLICATION

This application claims priority from U.S. Non-Provisional application Ser. No. 15/621,068, filed 13 Jun. 2017, from which this application is a Divisional Application.

TECHNICAL FIELD

This disclosure relates to an apparatus and method for collecting neurological data and, more particularly, a method and apparatus for analyzing neurocognitive data.

BACKGROUND

Minor head injury and concussion can cause neurological anomalies that may manifest via symptoms like loss of consciousness, amnesia, headache, dizziness, fatigue, and light sensitivity. These neurological anomalies may also or instead manifest via subtler symptoms like decreased neurocognitive function, impaired hand-eye coordination, and inhibited depth perception. Many other correlated neurocognitive functions are suspected of being causally related to minor head injury and concussion.

Modern traumatic brain injury testing solutions vary in scope of testing, portability, and price. Most modern testing solutions only measure a single facet of neurocognitive function at a time, while testing solutions that measure multiple neurocognitive functions in a single test are too expensive and cumbersome to reasonably allow for portability. These limitations naturally limit the locations and frequency with which the test can be administered, and the delay between the possible traumatic head injury and the administration of the test.

SUMMARY

In an aspect, a neurological data collecting apparatus is described. A plurality of electronically interconnected interface panels configured to selectively display stimuli and accept input is provided. An interface panel frame supports the plurality of interface panels and aggregates the plurality of interface panels into a user interface screen that extends into the user's peripheral vision when the user is standing within a predetermined distance from the user interface screen. A supporting stand is connected to the user interface screen. The supporting stand includes a height adjustment mechanism for adjusting the height of the user interface screen to eye level of the user. A control unit electronically connects the user interface screen to a computer.

In an aspect, a method for analyzing neurocognitive data is described. A portable user interface screen that extends into the user's peripheral vision on a supporting stand at a user's eye level and a computer electronically connected to both a data collection and aggregation system and a user interface screen via a control unit are provided. A neurocognitive test to be programmatically generated is sent from the computer to the user interface screen via the electronic connection to the control unit. At least one neurocognitive test is displayed on the user interface screen. Input from the user responsive to at least one neurocognitive test is accepted and recorded. Input is sent from the user interface screen through the control unit to the computer and from the computer to a data collection and aggregation system. The neurocognitive data derived from the input is analyzed using algorithms. Results are created responsive to the neurocognitive data. The results are sent from the data collection and aggregation system to the computer to be displayed on the computer in a user-perceptible format.

BRIEF DESCRIPTION OF THE DRAWINGS

For a better understanding, reference may be made to the accompanying drawings, in which.

DETAILED DESCRIPTION

Unless defined otherwise, all technical and scientific terms used herein have the same meaning as is commonly understood by one of skill in the art to which the present disclosure pertains.

As used herein, the term "user" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 1A:
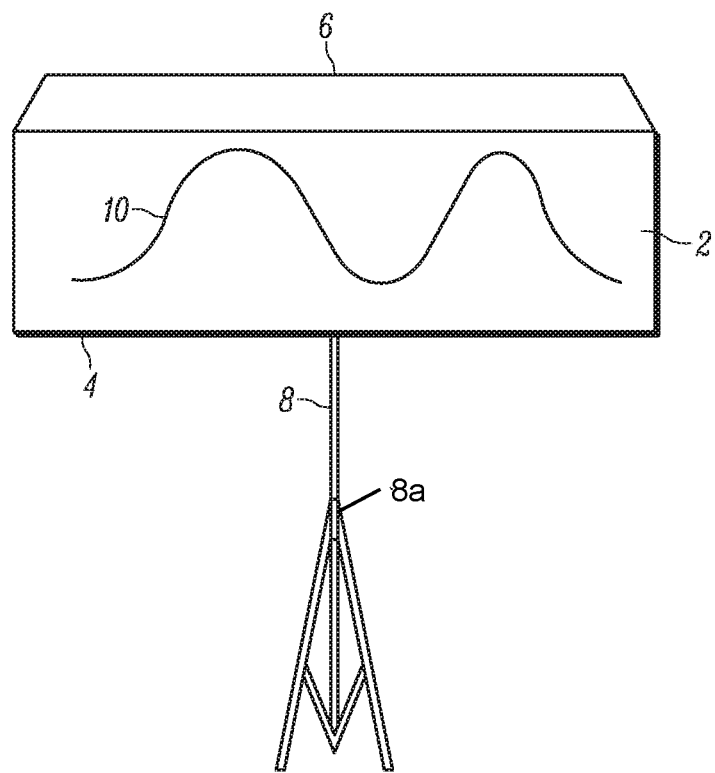
FIG. 1A schematically depicts a front view of an aspect of the apparatus.
Figure 1B:
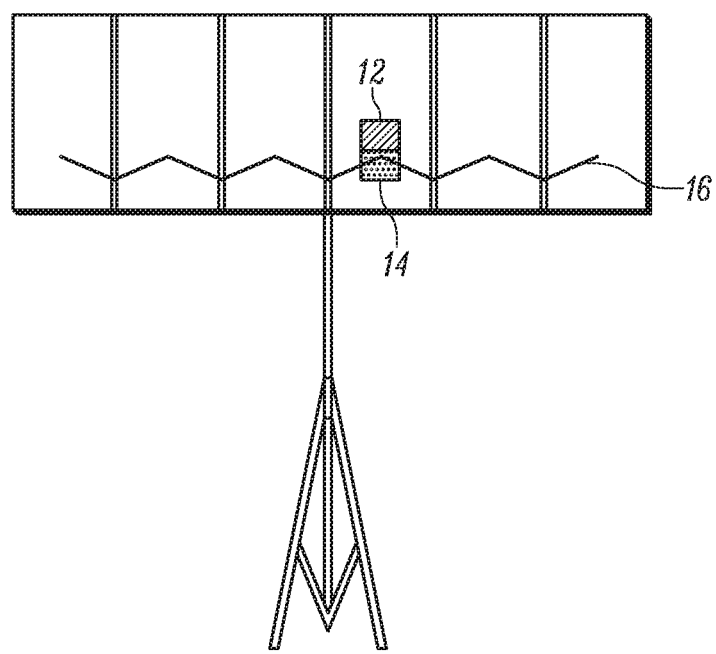
FIG. 1B schematically depicts a back view of the apparatus of FIG. 1A.

An apparatus for collecting neurological data from a user is shown in FIG. 1A and FIG. 1B. The apparatus uses a plurality of electronically interconnected interface panels 2 configured to selectively display stimuli, such as visual, tactile, or audible stimuli, and accept input, such as tactile, verbal, or visual input. Each interface panel 2 includes an electronically controlled stimulus display 18 and one or more corresponding input sensors 20 that may be associated with individual stimuli and the time the user interacted with that same individual stimuli. The electronically controlled stimulus display 18 may use liquid crystal display (LCD), light emitting diode (LED), organic light emitting diode (OLED), plasma display panel (PDF), or any other desired technology to create a two-dimensional video display that covers a substantial portion of the surface area of the front of the interface panel 2. (It is also contemplated that the display screen could be virtual, or augmented reality, such as by providing the user with a pair of virtual reality glasses or any suitable virtual reality headset and appropriate software/hardware to display stimuli and accept input in an analogous manner—in virtual space—to the use of the method and apparatus described and shown herein as occurring at least partially in physical space.) The input sensors 20 may use resistive touch screen, capacitive touch screen, surface acoustic wave, infrared grid, optical imaging technology, force sensors, buttons, or any other desired input or user interface component to measure where and when a user touches an interface panel 2. The user interface screen 6 could also or instead use speakers and/or a microphone to interact with the user when audible stimuli and/or verbal input are present in the apparatus.

Figure 2:
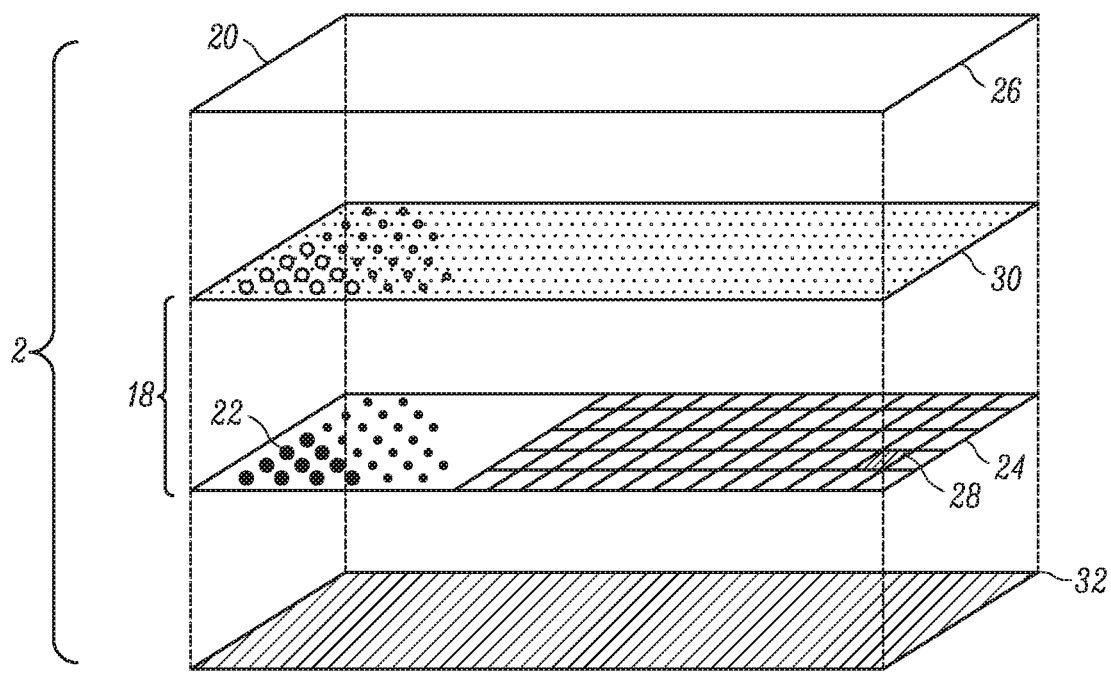
FIG. 2 is an exploded perspective schematic view of a component of the aspect of FIG. 1A.

As shown in FIG. 2, the interface panels 2 may each use a plurality of LEDs 22 soldered (or otherwise connected) to a printed circuit board 24 to create an electronically controlled stimulus display 18. Each LED 22 may be, for example, 5×5 mm, with a series of LEDs 22 arranged in any desired configuration, such as in a 16×28 matrix, on the printed circuit board 24. One example interface panel 2 uses a four-wire resistive touchscreen 26 that covers the entire stimulus display to create input sensors 20. The four-wire resistive touchscreen 26 could be connected to the printed circuit board 24 by a flexible printed circuit board or ribbon cable (not shown). The printed circuit board 24 contains an integrated circuit 28 which converts the input data into x and y coordinates in order to correspond the input with an associated individual stimulus. In between the printed circuit board 24 and the 4 wire resistive touchscreen 22 is a buffer plate 30 which is a material that fills the gaps between the LEDs 18, so the four-wire resistive touchscreen 26 is resting on a substantially level surface (the LEDs 18 and the buffer plate 30). Behind the printed circuit board 24 is a back plate 32, which is a metal plate that protects the printed circuit board 24.

The interface panels 2 each slide into an interface panel frame 4, which aggregates the interface panels 2 to form a user interface screen 6 that extends into the user's peripheral vison when the user is standing within a predetermined distance from the user interface screen, such as up to 20" away, from the user interface screen 6. (A user-to-screen separation of 20" or less has been shown to facilitate a desired field of vision, and of peripheral vision, for the user while still allowing the size of the user interface screen 6 to be relatively compact and thus portable, in some use environments of the present invention.)

For example, it is generally held in the field that peripheral vision begins at approximately 60 degrees from the center of the user's gaze. Therefore, a desired testing distance away from the screen can be calculated for a particular screen size based upon that 60-degree "rule of thumb". One of ordinary skill in the art will be able to specify sizing of a user interface screen 6, and corresponding placement of the user relative to the screen, to achieve the desired field of vision results for a particular use application of the present invention. It is contemplated, though, that the sizing, vertical placement in the field of view, horizontal placement in the field of view, and distance from the user of the user interface screen 6 may vary, depending upon the size, visual ability, and other characteristics of the user. Therefore, one of ordinary skill in the art will be able to configure a user interface screen 6 for a particular use environment and/or a particular user without undue experimentation, using the principles articulated herein along with the knowledge of one of ordinary skill in the art.

A functionally significant feature of the apparatus is that it uses a user interface screen 6 that extends into the user's peripheral vision. Any sized user interface screen 6 can measure peripheral vision based on how close user is to the user interface screen, but the closer a user is to the user interface screen, the more depth perception can be measured. A user interface screen that still extends into the user's peripheral vision when the user is, for example, up to 20" away results in a relatively large and wide user interface screen 6 that increases both the measurements of peripheral vision and depth perception as the user interface screen 6 width increases and the user's distance from the user interface screen 6 decreases. Stated differently, the closer a user is to the user interface screen 6, the more depth perception can be measured, while the further away a user is, the more of the user interface screen 6 is in an area of central vision.

Figure 3:
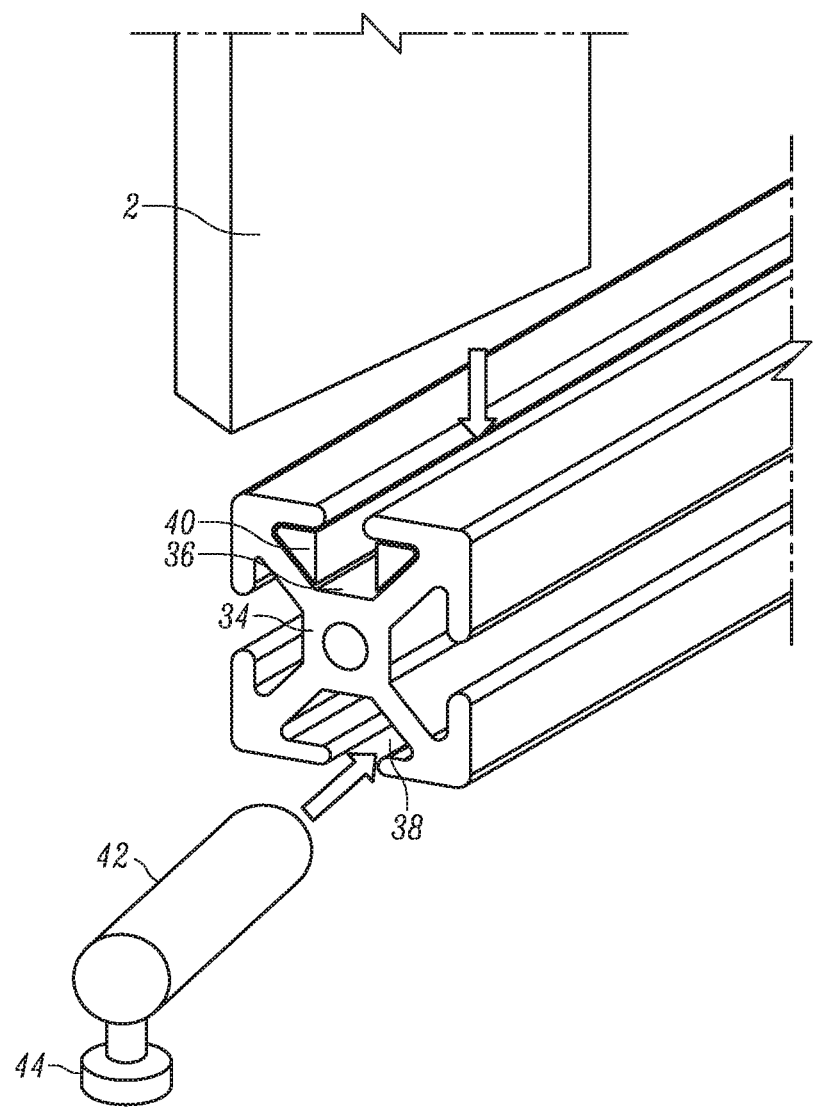
FIG. 3 is a detailed partial bottom perspective schematic view of a component of the aspect of FIG. 1A and FIG. 4A.

The interface panel frame 4 may be built, for example, from extruded aluminum bars 34 as shown in FIG. 3. As shown in FIGS. 1A and 1B, in one possible embodiment the interface panel frame 4 includes four extruded aluminum bars 34 formed into a rectangle. As shown in FIG. 3, the interior enclosed area 36 of each extruded aluminum bar 34 could have an adapter 40 to allow at least one interface panel 2 to be slid into the interior enclosed area 36, so as to allow the interface panels 2 to be combined using the interface panel frame 4 into the user interface screen 6.

Figure 4A:
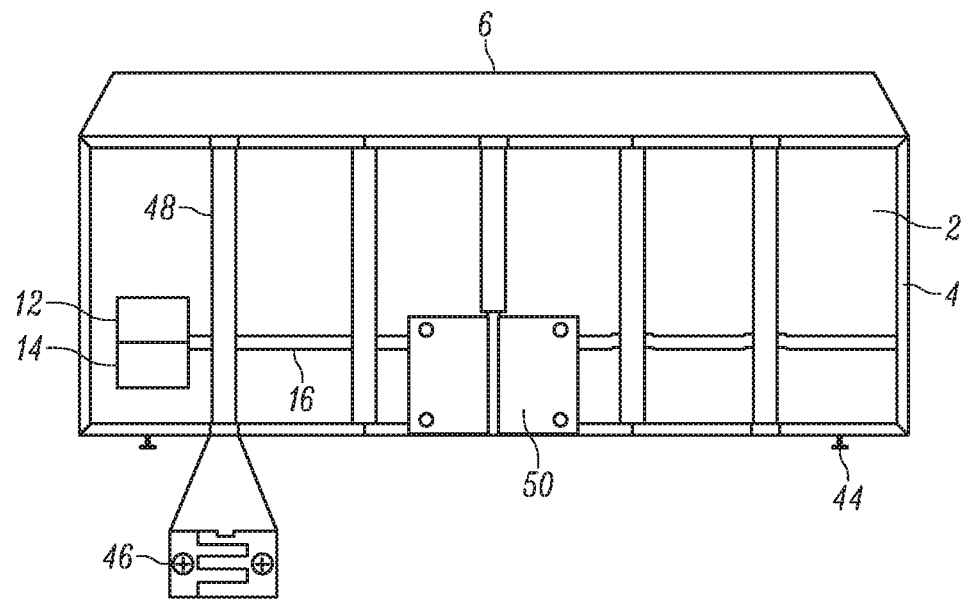
FIG. 4A is a schematic rear view of the aspect of FIG. 1A in an alternate configuration.
Figure 4B:
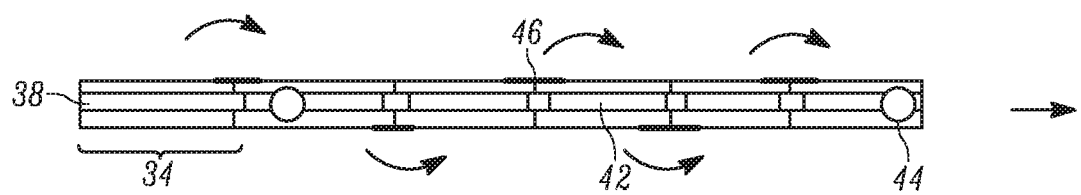
FIG. 4B is a schematic top view of the aspect of FIG. 4A.

As shown in FIG. 4A, in an alternate configuration of the interface panel frame 4 to that shown in FIGS. 1A and 1B, each interface panel 2 may attach to each adjacent interface panel 2 via at least one hinge 46, so that the plurality of interface panels 2 being aggregated into a user interface screen 6 are configured to fold in an accordion or map-like manner. As shown in FIG. 4B, the user interface screen 6 folds in an accordion or map-like manner when the last interface panel 2 folds inwards on the adjoining interface panel 2 followed by that interface panel 2 folding outwards on the next adjacent interface panel 2, which is then repeated until all interface panels 2 are collapsed on each other in a zigzag type manner in the horizontal direction. When the user interface screen 6 includes one or more "rows" of interface panels 2 stacked vertically, rather than the single row shown in FIG. 4A, then the user interface screen 6 could also or instead collapse in a similar zig-zag type manner in the vertical direction.

Figure 4C:
FIG. 4C is a schematic bottom view of the aspect of FIG. 4A.

In an example of this alternate configuration of FIGS. 4A-4C, the top and bottom of the interface panel frame 4 may include a plurality of extruded aluminum bars 34 that are each the same length as a corresponding attached interface panel 2. Each extruded aluminum bar 34 may be attached to an adjacent extruded aluminum bar 34 by hinges 46 with up to a 180-degree angle of rotation. As shown in FIG. 4C, when all hinges 46 are fully extended to 180 degrees, the extruded aluminum bars 34 and their corresponding attached interface panels 2 would become horizontally aligned with each other to form the aggregated user interface screen 6. As shown in FIGS. 3, 4B, and 4C within the exterior enclosed area 38 of the top and bottom extruded aluminum bars 34 are a plurality of rods 42, which may have any desired shape, including a contoured profile substantially matching that of the exterior enclosed area 38. For example, a number of rods 42 equal to one fewer than the number of interface panels 2 could be provided. The leftmost and rightmost rods 42 have knobs 44 attached to them. When the knobs 44 are slid along the top of the user interface screen 6, all of the rods 42 are shifted either left or right within the exterior enclosed area 38, in accordance with the sliding direction of the knobs 44. As shown in FIG. 4C, when the rods 42 are shifted halfway to the left or right, each rod 42 spans two adjacent extruded aluminum bars 34, thus bridging across the hinged connection and creating a lock to prevent relative pivoting of those adjacent interference panels 2 with respect to each other. As shown in FIG. 4B, when the pins 36 are shifted completely left or right, the rods 42 only span their respective extruded aluminum bars 34 and align with the corresponding interference panels 2 between the hinges 46, thus allowing the rotation of each interface panel 2 towards an adjacent interface panel 2 in facilitating folding of the user interface screen 6, with an entirely self-contained system which does not require additional, separate locking components for use.

Each interface panel 2 is electronically connected to an adjacent interface panel 2, to a control unit 12, and to a power supply 14. The control unit 12 controls the stimuli display of the interface panels 2 and accepts the input from the interface panels 2. The control unit 12 may be an embedded single board computer controller with microprocessor(s), memory, input/output (I/O) and other features found in a functional computer (which is used herein to reference any desired type of computer structure, including a micro control unit). The power supply 14 is an electronic power distributor that supplies the power to each interface panel 2 and the control unit 12. The power supply 14 can connect to any AC adapter, AC/DC adapter, or AC/DC converter power cord, such as a power cord typically used to charge a laptop or to an external battery, and/or the power supply 14 could include its own onboard battery or other power storage feature.

The control unit 12 and power supply 14 may be physically attached to any interface panel 2. In the configuration of FIGS. 1A-1B, where each interface panel 2 is separate from the others until assembled for use, the interface panels 2 may be electronically connected to each other by a user during assembly using electronic connectors 16 (FIG. 4) like a ribbon cable, a flexible printed circuit board, rigid ports/sockets, or any other desired electrical connecting feature. In the configuration of FIGS. 4A-4C, where each interface panel 2 is always connected with an adjacent interface panel 2 during storage, transport, and use, the electronic connectors 16 may be, for example, a permanent flexible printed circuit board, and a flexible protective shield 48 may be placed between each pair of adjacent interface panels 2 to protect the electronic connectors 16.

The control unit 12 may be electronically connected to a computer 12. The computer 12 may be a desktop computer, a laptop computer, a tablet computer, a smartphone, a hand-held computer device, or any other desired computer component. The computer 12 may be electronically connected to the control unit 12 by a wired or wireless personal area network (PAN) technology such as, but not limited to, BLUETOOTH® (IEEE 802.15.1 specification), USB cable, Wireless USB, or ZIGBEE® (IEEE 802.15.4 specification); by a wired or wireless local area network (LAN) technology such as, but not limited to, an Ethernet cable or Wi-Fi® (Wireless Fidelity); and/or by radio frequency (RF) and/or wide area network (WAN) technologies such as, but not limited to, digital radio and remote Internet.

A supporting stand 8 with a height adjustment mechanism 8a may connect to the interface panel frame 4 or directly to the user interface screen 6. The height adjustment mechanism 8a, when present, allows for adjustment of the user interface screen 6 to the user's eye level. That is, the supporting stand 8 may be an adjustable stand that has a variable height above the ground corresponding to the placement of the user interface screen 6 at eye level of the user. Alternately, the supporting stand 8 may be a flat display mounting interface or other wall adapter (e.g., like those sometimes used to mount flat-screen TVs to an upright surface) that is adjustably attached to a vertical surface and configured to allow the user interface screen 6 to be moved up and down to correspond to eye level of the user. In the configuration shown in FIGS. 1A-1B, the supporting stand 8 may attach directly to the bottom extruded aluminum bar 34. As shown in the configuration of FIGS. 4A-4C, the back of the interface screen 6 could contain a mount interface, such as a standard VESA mount (Video Electronic Standard Association, Mounting Interface Standard), thus allowing any VESA-compatible stand or wall mount to be used as a supporting stand 8. A flat display mounting interface that is adjustably attached to a vertical surface is not limited to just a wall mount, but may also include supporting stand 8 designs compatible with the trailer hitch of a vehicle, a crossbar of audience seating bleachers, a tailgate of a vehicle, or any other relatively stationary surface in front of which a user can stand during use of the apparatus. One of ordinary skill in the art can readily provide a suitable supporting stand 8 design for a desired use environment of the present invention.

Another configuration of the apparatus could use one OLED stimulus display as the user interface screen 6, rather than a plurality of interface panels 2. Due to the flexibility of the OLED stimulus displays, the user interface screen 6 would be able to be rolled up or folded without the need for separate interface panels 2. A carbon fiber lattice support, or any other desired framing or mounting components, may be attached to the user interface screen 6 to support its weight, hold the OLED stimulus display in a desired steady position for use of the apparatus, and/or provide an attachment mechanism to the supporting stand 8.

It is contemplated that, when an OLED stimulus display is used as the user interface screen 6, the OLED stimulus display could be curved to at least partially laterally surround the user and thus keep the user interface screen 6 surface at a substantially constant distance from a stationary user.

However accomplished, though (via a folding structure, a flexible OLED, a virtual reality interface, or any other desired scheme), the portability of the user interface screen 6 may be important for some use environments (e.g., beside a playing field), in order to facilitate rapid and frequent testing of users.

As an example, a user interface screen 6 as described herein and shown in the Figures may be approximately 2'×6'×0.5" in a use configuration and approximately 2'×1'×3" as packed for transport/storage.

Figure 5:
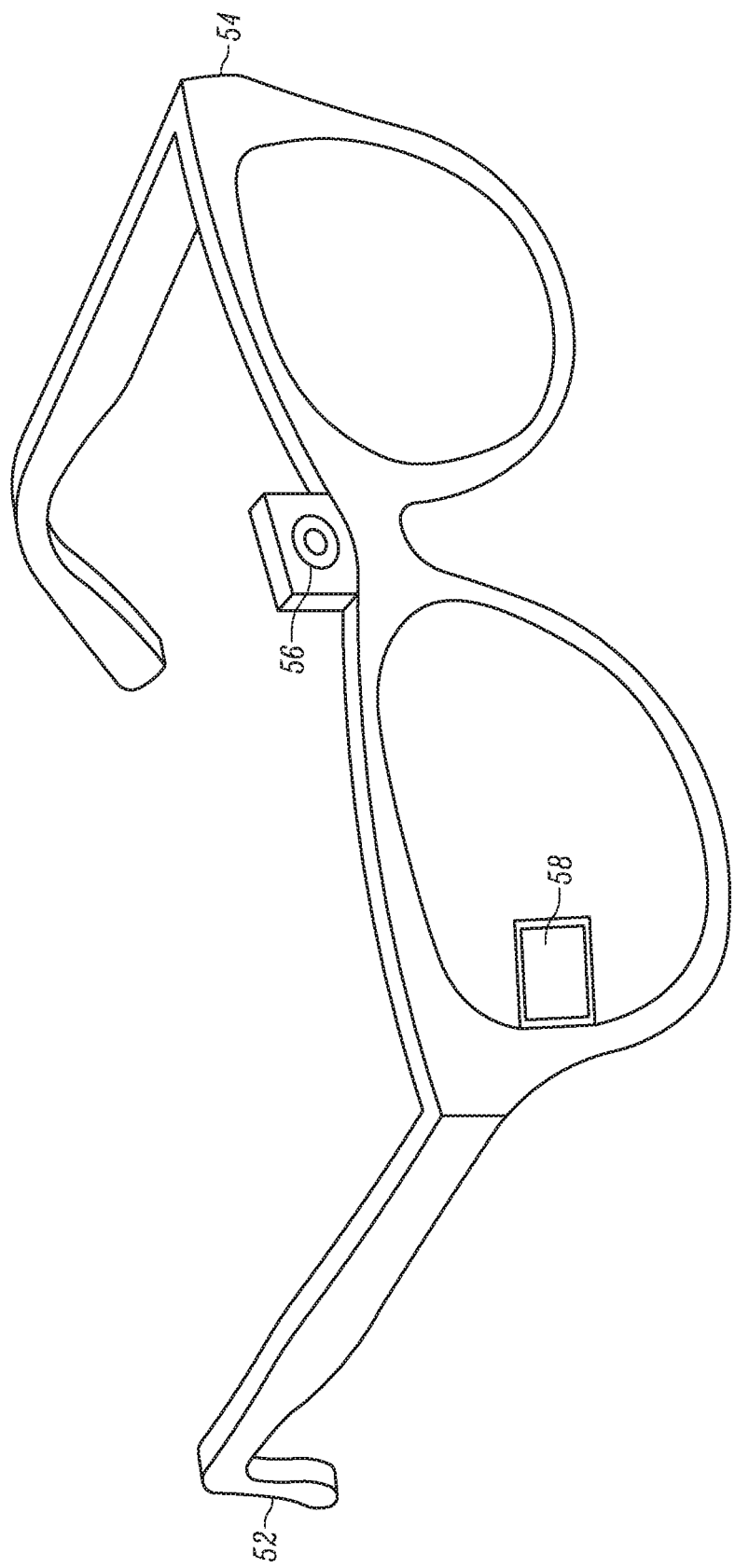
FIG. 5 is a schematic front view of a component of an alternative configuration.

The apparatus may also include at least one external sensor 52 in addition to the input sensors 20 as shown in FIG. 5 that records tactile, visual, or audio sensations generated by the user or the environment. An external sensor 52 could be attached to the user interface screen and electronically connected to the computer or the control unit 12 via a direct electronic connection to the control unit 12 or indirect connection to an interface panel 2. At least one of the external sensors 52 may be a camera configured to record at least one of the user's eye and body movements. As shown in FIG. 5, a plurality of external sensors in the form of cameras may be a placed on a pair of glasses 54 the user would wear while interacting with the user interface screen 6. When a plurality of cameras are provided, one camera could be a video camera 56 that records the user interface screen 6 in order to record what stimulus the user is looking at, and another camera could be an infrared camera 58 recording the pupil movements of the user. Another configuration could attach a video camera to the user interface screen 6, pointed toward the user, in order to record the user's body movements. Additional external sensors (e.g. thermometer, pulse oximeter, and/or barometer; not shown) could be associated with the user interface screen 6 and by extension the control unit 12 to collect additional environmental, physiological, and/or health data such as, but not limited to, body temperature, pulse, blood pressure, blood oxygen, ambient temperature, light, atmospheric pressure, lactic acid levels, and/or heart rate.

The user interface screen 6, interface panel frame 4, and supporting stand 8 may be configured for repeated disassembly and reassembly by the user. The versatility and design of these structures makes the apparatus portable, which allows for the apparatus to be used in any environment. In the rectangular interface panel frame 4 configuration of FIGS. 1A-1B, the apparatus may be assembled by a single user in less than ten minutes by first constructing the interface panel frame 4, attaching the supporting stand 8 to the interface panel frame 4, sliding the interface panels 2 into the interface panel frame 4, and electronically connecting the interface panels 2 to each other. In the FIGS. 4A-4C configuration using the accordion design, or the OLED stimulus display (not shown), the apparatus can be assembled in less than one minute by first extending the user interface screen 6, and then attaching the supporting stand 8 to the VESA mount interface 50 or another mount interface associated with the user interface screen 6.

Figure 6:
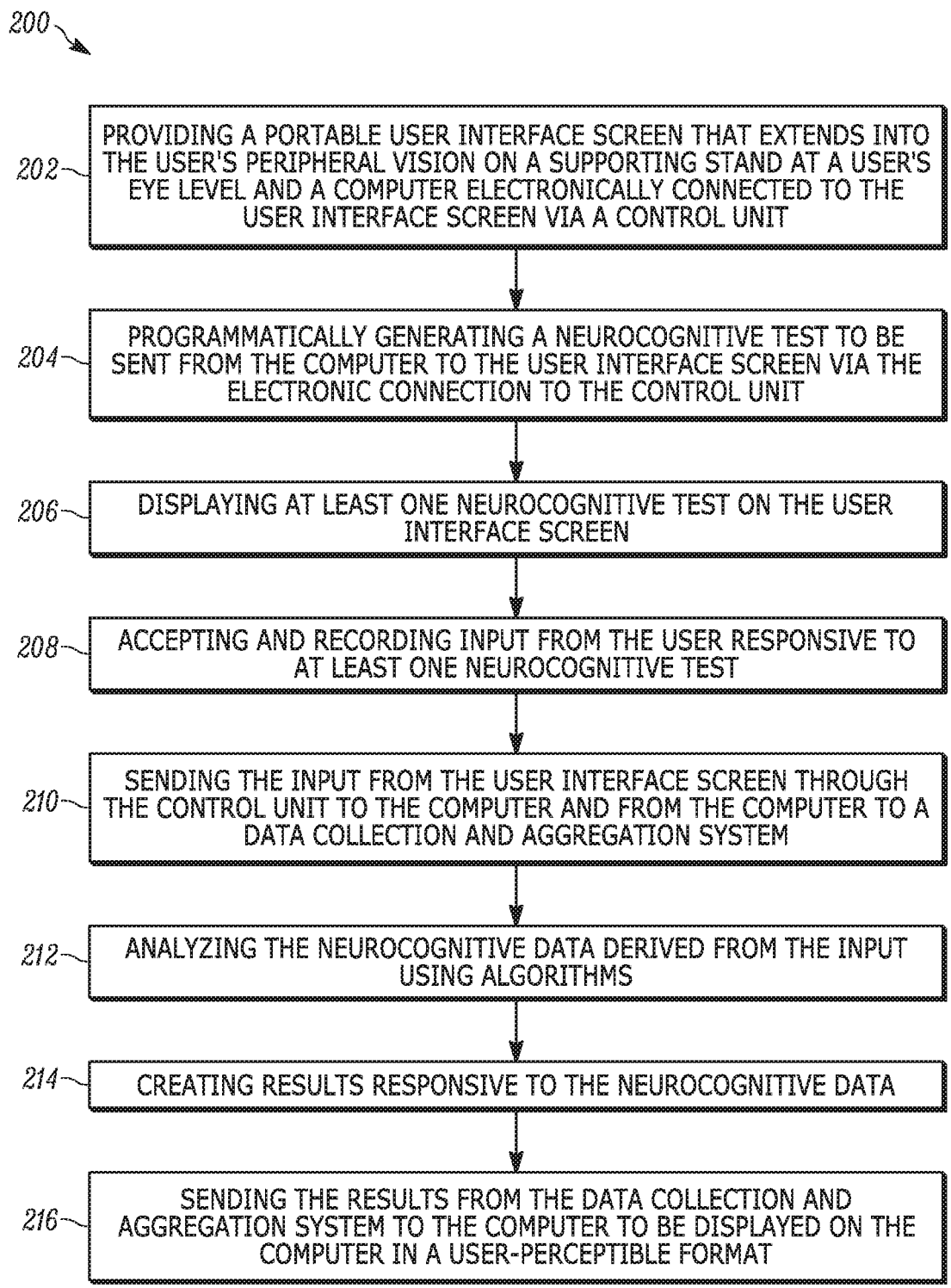
FIG. 6 is a flow chart of a method for using the aspect of FIG. 1.

The apparatus and system described herein analyzes neurological data derived from the input a user by using a method as shown in a flow chart 200 in FIG. 6 In a first action block 202 of the flow chart 200, a portable user interface screen 6 is provided. The user interface screen 6 extends into the user's peripheral vison when the user is standing within a predetermined distance from the user interface screen 6, and uses a supporting stand 8 to be at a user's eye level. Optionally, additional external sensors (e.g. thermometer, pulse oximeter, and/or barometer; not shown) could be associated with the user interface screen 6 and be used in the method described herein to collect additional environmental, physiological, and/or health data such as, but not limited to, body temperature, pulse, blood pressure, blood oxygen, ambient temperature, light, atmospheric pressure, lactic acid levels, and/or heart rate. This additional data can be used in any desired manner to inform, weight, control for, or otherwise affect the test results, and/or could simply be recorded for the record, as desired.

In a second action block 204 of the flow chart 200, a computer 12 electronically connected to both a data collection and aggregation system 14 (e.g., a computer server, optionally including a database function) and the user interface screen 6 via the control unit 12 is provided. The data collection and aggregation system 14 may be either remote internet-connected cloud based data collection and aggregation system or a local data collection and aggregation system held on the computer 12.

In the third action block 206 of flow chart 200, the computer 12 sends a programmatically generated neurocognitive test 10 (FIG. 1A) to the user interface screen 6 via the control unit 12. Every neurocognitive test 10 is programmatically generated according to a series of preset algorithmic rules located in the computer, data collection and aggregation system, and/or control unit. In the fourth action block 208 of flow chart 200, the user interface screen 6 displays at least one neurocognitive test 10, accepts the user's responses to said neurocognitive test 10, and records them as input. A neurocognitive test 10 is sequences of stimuli displayed on the user interface screen 6, where the reactions of the user to such sequences of stimuli (represented by a sinusoidal line in FIG. 1A) are correlated with at least one of the neurocognitive data types being chosen from data types including, but not limited to, psychomotor response, complex reaction time, memory, balance, peripheral awareness, and/or any other desired neurocognitive data type.

Psychomotor response is a response involving both the brain and motor activity. Psychomotor response of a user can include measurable parameters such as simple reaction time, peripheral awareness, and depth perception. Simple reaction time can be measured using the user interface screen 6 by measuring the time it takes for a user to recognize a stimulus and interact with it. A neurocognitive test 10 (FIG. 1A) can also measure at least one of a peripheral awareness and/or depth perception of the user responsive to the presence of the user interface screen 6 in the user's peripheral vision. Peripheral awareness can be measured using the user interface screen 6 by the location accuracy of a user's interaction with stimuli at least approximately 60 degrees to the left or right of a user's forward line of sight, in accordance with the conventional definition of "peripheral vision", as previously discussed. Optionally, the apparatus can detect and monitor the user's forward line of sight, in order to facilitate the measurement of peripheral awareness. Depth perception can be measured using the user interface screen 6 by measuring the location accuracy of a user's interaction with stimuli that is large distance away from the user. As the user interface screen 6 size increases, the distance between the user and the farthest possible stimuli also increases (for a flat, not curved, screen), thus, the ability to measure depth perception increases. The user interface screen 6 and related components of the apparatus therefore allow the neurocognitive test 10 to help to measure and directly characterize a user's psychomotor ability responsive to measurements of simple reaction time, peripheral awareness, and depth perception.

Complex reaction time can be measured using the user interface screen 6 by the time it takes for a user to recognize a stimulus, decide whether to interact with the stimulus, and then interact with the stimulus. Memory can be measured using the user interface screen 6 by the display of a sequence of stimuli and subsequent measurement of the accuracy by which the user repeats that sequence of stimuli through input. If the apparatus uses a video camera to track eye movement by obtaining and recording video input of the user responding physically to the neurocognitive test 10 (FIG. 1A), then the neurocognitive test 10 may indirectly characterize a user's balance ability responsive to measurements of at least one of eye movement, peripheral awareness and depth perception, because measurements of vision can be correlated with the neurocognitive data type of balance. In addition, other sensors added to the apparatus (e.g. thermometer, pulse oximeter, and/or barometer) may be used to generate environmental or other health data types.

In the fifth action block 210 of flow chart 200, the user interface screen 6 sends the input to the computer 12 via the control unit 12. Input may include data collected from input sensors 20 and multiple types of external sensors 52 that record tactile, visual, and/or audio sensations generated by the user or the environment. In the sixth action block 212 of flow chart 200, the computer 12 sends the input to the data collection and aggregation system 14. In the seventh action block 214 of flow chart 200, the data collection and aggregation system 14 analyzes the neurocognitive data derived from the input using algorithms and creates results responsive to that neurocognitive data 18. In the eighth action block 216 of flow chart 200, data collection and aggregation system 14 sends these results 18 to the computer 12, and the computer 12 displays the results 18 in a user-perceptible format to the user.

Figure 7:
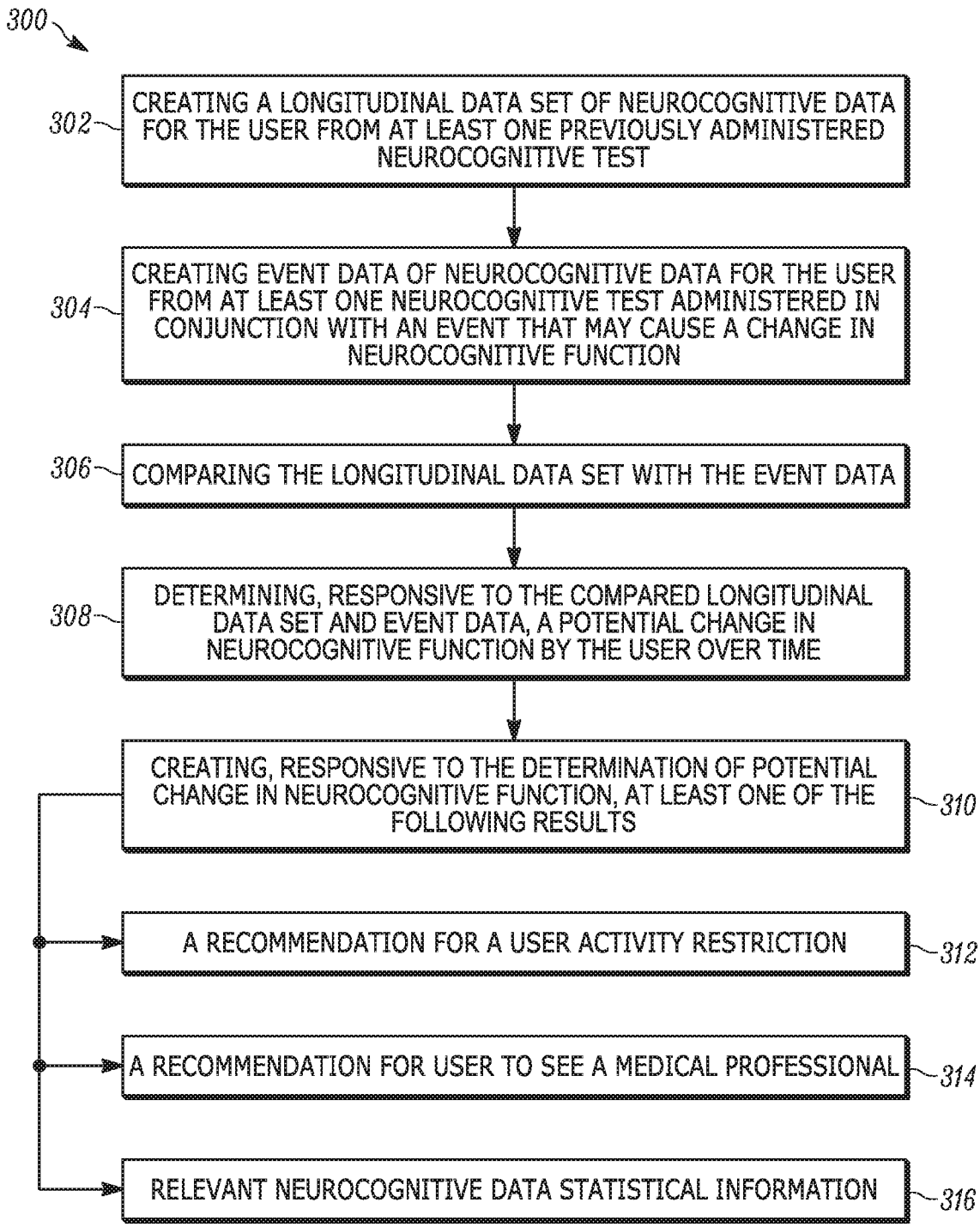
FIG. 7 is a flow chart of a method for creating an aspect in FIG. 6.

The data collection and aggregation system may create results responsive to neurocognitive data by using a method as shown in a flow chart 300 in FIG. 7. In the first action block 302 of flow chart 300, the data collection and aggregation system creates a longitudinal set of neurocognitive data for the user from at least one neurocognitive test 10 (FIG. 1A), each of which may be taken at any time during the user's involvement with the apparatus and method of the present invention. The neurocognitive tests 10 could be taken frequently throughout the year by the user in order to create a baseline and rich history of information regarding neurocognitive function for that user. The portability of the user interface screen 6 also allows for a more accurate and robust longitudinal data set because the neurocognitive tests 10 can be easily taken more often. Since the neurocognitive tests 10 can be administered wherever the user is located, there are many opportunities to run many neurocognitive tests 10, either in the regular course of the activity, or in response to some suspected trauma event.

In the second action block 304 of flow chart 300, the user creates event data from at least one neurocognitive test 10 administered at any time, and for any reason. For the purpose of the below description, the flow chart 300 presumes that the neurocognitive test 10 which is being compared—as event data—to the longitudinal data set (of at least one previously administered neurocognitive test 10) is administered in conjunction with (e.g., directly after) an event that may cause a change in neurocognitive function (as opposed to just being administered to the user at a random time). The neurocognitive test 10 may be administered at any time, and without regard to whether a change in neurocognitive function is suspected. For example, a "standing" weekly (or other periodically-administered) neurocognitive test 10 could be given to help detect latent neurocognitive damage which does not arise to a level of severity sufficient to come to the attention of a user or observer otherwise.

An event that may cause a change in neurocognitive function could be a suspected concussion, such as the user taking a significant blow to the head. For example, during a football game a user may be involved in a violent head-to-head collision that a medical trainer suspects may have caused a concussion. That user could be taken out of the game, and immediately be administered a neurocognitive test 10 (FIG. 1A), which would then be used as event data in the aforementioned comparison.

Another event that may cause a significant change in neurocognitive function could be the beginning or conclusion of an event where a concussion may occur. The neurocognitive test 10 (FIG. 1A) could be administered at some point in time tied to the timing of that event as a matter of course, even if there is no suspicion that a change in neurocognitive function actually did occur. For example, a user could play an entire game of football where they sustained multiple sub-concussive events, which could even be unsuspected or unnoticed by the team's medical trainers. After the conclusion of the game, if the user takes a neurocognitive test 10 for event data as a matter of post-game protocol, the apparatus could help determine if such micro concussions (or even impacts which do not rise to the level of a concussion) during the course of that game likely caused a significant decrease in neurocognitive function. For the sake of description, the term "a concussion" is used herein to encompass both a single impact event and a series of sub-concussive events.

Another event that may cause a change in neurocognitive function could be period of restricted activity. For example, if a user is "benched" from practice/games or otherwise restricted from activity, a neurocognitive test 10 (FIG. 1A) could be used to produce a set of event data, with the event being the nonparticipation of the user. Use of such event data could help detect gain of neurocognitive function related to recovery from trauma. It is contemplated that the neurocognitive test 10 for the production of event data could be administered at any time, and for any reason (or no particular reason), as desired by the user and/or coach/staff or other personnel. For example, the neurocognitive test 10 could be administered weekly, whether or not a game or practice has occurred. Because the neurocognitive test 10 is administered in an effort to detect potential neurocognitive function change, regularly scheduled testing (regardless of a user's activity status) should be considered to fall under the category of "an event that may cause a change in neurocognitive function".

The event data produced in, for example, the latest administered neurocognitive test 10 (FIG. 1A) could be compared to any desired one or more—up to all—of the longitudinal data set produced by the at least one neurocognitive test 10 previously administered to that user. Additionally, or alternatively, the event data from any chosen one of a series of neurocognitive tests taken by a user could be compared to the data set of information produced by any other one or more neurocognitive tests in the series, for any desired reason.

The portability and quick assembly/disassembly of the user interface screen 6 allows for more accurate and timely event data to be taken immediately after a suspected concussion or the conclusion of an event where a concussion may have occurred, because the user interface screen 6 could be located nearby for ease of prompt access related to any event where a concussion may occur, or where immediate post-game data is desirable.

In the third action block 306 of flow chart 300, the data collection and aggregation system uses algorithms to compare the event data with the longitudinal data set. In the fourth action block 308 of flow chart 300, the data collection and aggregation system determines responsive to the comparison if there was potential change in neurocognitive function over time. In the fifth action block 310 of flow chart 300, the data collection and aggregation system creates results responsive to the potential change in neurocognitive function of the user. In the sixth action block 312-316 of the flow chart, the results may take the form of a recommendation for a user activity restriction 312, a recommendation for the user to see a medical professional 314, and/or relevant neurocognitive data statistical information 316. The results 18 may be used by team medical trainers to make decisions like restricting (or choosing not to restrict or to remove a previous restriction) user activity and/or recommending that the user see a medical professional. The results 18 may be used by team personnel, the user, medical professionals, or any other party to make decisions including diagnosing potential or actual trauma-related medical issues, restricting a user's activities, providing medical treatment, determining recovery time and/or any other reason.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

What is claimed is:

1. A touch screen display providing a neurological data collecting apparatus, comprising:
    a plurality of electronically interconnected collapsible interface touch screen display panels configured to selectively display stimuli and accept input;
    a touch screen display frame supporting the plurality of touch screen display panels and having an aggregated plurality of touch screen display panels forming a touch screen display that is portable and that extends at least 60 degrees from a center of the user's gaze into the user's peripheral vision when the user is within a predetermined distance from the touch screen display;
    a supporting stand connected to the touch screen display, including a height adjustment mechanism for adjusting the height of the touch screen display to eye level of the user; and
    a control unit electronically connecting the touch screen display to a computer, the touch screen display providing an unbounded, except for the frame, tactile area providing locational accuracy and non-predisposed positional data and a user's hand touching the touch screen display at a precise location on the tactile area to record the user's reaction time and positional data in response to the stimuli.

2. The apparatus as set forth in claim 1, wherein each touch screen display includes an electronically controlled stimulus display and corresponding input sensors that may be associated with individual stimuli.

3. The apparatus as set forth in claim 2, wherein the touch screen display includes a plurality of LEDs embedded into a printed circuit board and the input sensors include a resistive touch screen that covers the entire touch screen display.

4. The apparatus as set forth in claim 1, wherein each touch screen display panel attaches to at least one other touch screen display panel via at least one hinge, and the plurality of touch screen display panels being aggregated into a tactile area configured to fold in at least one of an accordion manner and a map-like manner.

5. The apparatus as set forth in claim 1, wherein the touch screen display comprises at least one organic light-emitting diode (OLED) flexible display.

6. The apparatus as set forth in claim 1, wherein computer is at least one of a desktop computer, a laptop computer, a tablet computer, a smartphone, and
    a hand-held computer device.

7. The apparatus as set forth in claim 1, wherein the computer may be electronically connected to the control unit by at least one of a wired or wireless personal area network (PAN); local area network (LAN) technology; radio frequency (RF) technology; and wide area network (WAN) technology.

8. The apparatus as set forth in claim 1, wherein the supporting stand is an adjustable stand that has a variable height above the ground corresponding to the placement of the touch screen display at eye level of the user.

9. The apparatus as set forth in claim 1, wherein the supporting stand is a flat display mounting interface that is adjustably attached to a vertical surface to allow the user interface screen to be placed at eye level of the user.

10. The apparatus set forth in claim 1, including at least one or more external sensors that records tactile, visual, or audio sensations generated by the user or the environment.

11. The apparatus set forth in claim 10, wherein at least one of the external sensors is a camera configured to record at least one of the user's eye and body movements.

12. The apparatus set forth in claim 1, wherein the touch screen display and supporting stand are configured for repeated disassembly and reassembly by the user.

13. The apparatus set forth in claim 1, including at least one external sensor for collecting at least one environmental, physiological, and/or health data including one or more of body temperature, pulse, blood pressure, blood oxygen, ambient temperature, light, atmospheric pressure, lactic acid levels, and heart rate.

14. A panel for receiving neurocognitive data, comprising:
a collapsible and portable user interface touch screen display bounded by a frame, the touch screen display having a width that extends into a user's peripheral vision by having the touch screen display extending from 60 to 120 degrees from a center of the user's gaze;
the touch screen display mounted on a support stand at the user's eye level and a computer electronically connected to the touch screen display via a control unit, the touch screen display comprising a tactile area having touch sensing capacity;
the touch screen display for receiving at least one stimulus via the electronic connection to the control unit;
the control unit measuring and recording tactile input including where and when the user touches the touch screen display via the hand of the user, responsive to the at least one stimulus, the touch screen display providing locational accuracy and positional data;
a data collection and aggregation system for receiving the input from the touch screen display and creating results responsive to the input.

15. The panel of claim 14 wherein the positional data is received via input to the tactile area of the touch screen display and not via a mechanical button.

16. The panel of claim 14 wherein the touch screen display is an aggregation of multiple touch screen displays.

17. The panel of claim 14 wherein the width extends at least 60 degrees from the center of the user's gaze.

18. The panel of claim 14, wherein the user touch screen comprises at least one organic light-emitting diode (OLED) flexible display.

19. The panel of claim 14, wherein computer is at least one of a desktop computer, a laptop computer, a tablet computer, a smartphone, and a hand-held computer device.

20. The panel of claim 14 wherein the stimuli are measured to determine whether the user has suffered a concussion.

* * * * *